United States Patent
Kysilka et al.

(10) Patent No.: US 10,017,532 B2
(45) Date of Patent: Jul. 10, 2018

(54) PLATINUM (IV) COMPLEX WITH INCREASED ANTI-TUMOR EFFICACY

(71) Applicant: VUAB PHARMA A.S., Roztoky (CZ)

(72) Inventors: Vladimir Kysilka, Prague (CZ); Jen Mengler, Prague (CZ); Karel Havlovic, Prague (CZ); Petr Kacer, Prague (CZ); Libor Cerveny, Prague (CZ)

(73) Assignee: Vuab Pharma A.S., Roztoky (CZ)

( * ) Notice: Subject to any disclaimer, the term of this patent is extended or adjusted under 35 U.S.C. 154(b) by 0 days.

(21) Appl. No.: 15/329,522

(22) PCT Filed: Sep. 3, 2014

(86) PCT No.: PCT/EP2014/068672
§ 371 (c)(1),
(2) Date: Jan. 26, 2017

(87) PCT Pub. No.: WO2016/034214
PCT Pub. Date: Mar. 10, 2016

(65) Prior Publication Data
US 2017/0226143 A1 Aug. 10, 2017

(51) Int. Cl.
*C07F 15/00* (2006.01)
*A61K 31/282* (2006.01)
*A61K 9/48* (2006.01)

(52) U.S. Cl.
CPC ........ *C07F 15/0093* (2013.01); *A61K 9/4858* (2013.01); *A61K 31/282* (2013.01)

(58) Field of Classification Search
CPC .................. C07F 15/0093; A61K 31/282
See application file for complete search history.

(56) References Cited

U.S. PATENT DOCUMENTS 6,503,943 B1   1/2003 Zak et al.

FOREIGN PATENT DOCUMENTS

| CZ | WO 99/61451 A1 | 12/1999 |
| EP | 0328274 A1 | 1/1989 |
| WO | WO2014/100417 A1 | 6/2014 |

OTHER PUBLICATIONS

International Search Report—PCT/EP2014/068672.
Fernande D. Rochon, et al. ("Synthesis and Characterization of Platinum (II) Complexes with Adementanamine Derivatives and Related Ligands"), Inorg, Chem., (contd. from above) 2;2717-2723 (1993).
Jana Kiasparkova, et al. ("Molecular Aspects of Antitumor Effects of a New Platinum (IV) Drug"), Mol. Pharm. 70:170819 (2006).
Office Action dated Feb. 21, 2018 for Russian Patent Application No. 201710914204 filed on Mar. 9, 2014 by Vuab Pharma a.S., Cz.

*Primary Examiner* — Joseph R Kosack
(74) *Attorney, Agent, or Firm* — Offit Kurman, P.A.; Robert D. Katz, Esq.

(57) ABSTRACT

The invention relates to a new platinum (IV) complex with substantially increased antitumor efficacy. The invention further discloses a process for preparing of said complex and a pharmaceutical composition for the therapy of tumor diseases containing said complex.

15 Claims, No Drawings

PLATINUM (IV) COMPLEX WITH INCREASED ANTI-TUMOR EFFICACY

FIELD OF THE INVENTION

The invention relates to a new platinum (IV) complex with substantially increased antitumor efficacy. The invention further discloses a process for preparing of said complex and a pharmaceutical composition for the therapy of tumor diseases containing said complex.

BACKGROUND OF THE INVENTION

The platinum (II) complexes, e.g. cisplatin, carboplatin or oxaliplatin, are broadly and long term used cytostatics (further CTS) in the therapy of tumor diseases. Their advantages are very good clinical experience and good antitumor efficacy. A big advantage of platinum CTS is that they kill already existing cancer cells by a direct cross-linking of their cellular DNA, in particular on guanine sites. Further, platinum CTS induce activation of stress kinases, resulting in increased expression of death receptors on the cell surface and increased transcription and translation of soluble death ligand (FAS ligand). This leads to activation of the external receptor apoptotic pathway. Platinum CTS, which preferentially binds to guanine, also inhibits telomeres having frequent sequences TTAGGG rich on guanine. Effects of platinum CTS are therefore surprisingly pluripotent and they are particularly suited to combination therapy of cancer with other CTS agents, including targeted inhibitors of cell signaling pathways. The drawbacks of platinum (II) CTS stem from the same action on cellular DNA in both cancer and healthy cells which result in serious side effects and toxicity. There is also impossibility of oral administration due to their big reactivity and less stability after administration. There is also described an acquired resistance of tumors against cisplatin after its long term use.

The platinum CTS as well as other CTS including targeted inhibitors are xenobiotic and they are rapidly captured, destroyed and eliminated by immune and enzyme systems after their administration to the body. A small residual portion of the administered dosage reaches the targeted cancer tissue as a consequence. So, the improvement of stability of the platinum CTS is of utmost importance. Further, a lipophilic cell membrane fundamentally limits penetration of any drug including platinum CTS into the cell and only a part of the residual portion of the dosage reaches the intracellular environment. Since a DNA-cross linking mechanism of action of the platinum CTS requires entry to cells, the capability of the platinum CTS to cross lipophilic cell membranes is of utmost importance. Once the part of the residual portion of the dosage reaches the intracellular environment, it is concurrently with its therapeutic action reduced and destroyed by the enzyme system with glutathione and degraded metabolites are then removed from the cells by the increased efflux by means of p-glycoprotein. Hence, the therapeutic efficacy of the platinum CTS and its degradation and elimination from the body after its administration is a kinetic competition variable in time.

The platinum (IV) complexes are a relatively new class of platinum anticancer drugs which offer unlike platinum (II) complexes better stability, increased lipophility, less toxicity and oral administration possibility. They also overcome a tumor resistance to cisplatin. The most interesting antitumor efficacy has platinum (IV) complex of the general formula (I) with cis,trans,cis geometric configuration of ligands around central Pt (IV)-ion:

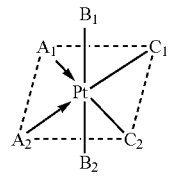

$A_1$ and $A_2$ are equatorial aminoligands which remain in the platinum complex. $B_1$ and $B_2$ are axial ligands which should be reduced to platinum (II) species in the intracellular environment. $C_1$ and $C_2$ are equatorial leaving ligands which are hydrolyzed to reactive aqua-platinum (II) species which then create firm cross-linked complexes with cellular DNA, in particular on guanine sites, which leads to the cell apoptosis.

In further text and examples of embodiment, the "c-t-c" abbreviation is used for "cis-trans-cis" configuration of ligands in order to specify the stereochemistry of ligands around the central Pt (IV)-ion when grouped pairwise in the order written. Basic information about optimized structures of "c-t-c" platinum (IV) complexes, about their antitumor efficacy and about a process for preparation of such complexes are described e.g. in EP 0 328 274 (Johnson Matthey, Inc.), EP 0 423 707 (Bristol-Myers Squibb Co.) and U.S. Pat. No. 6,503,943 (Lachema, a.s.).

The most promising "c-t-c" platinum (IV) complex in the prior has the formula (II):

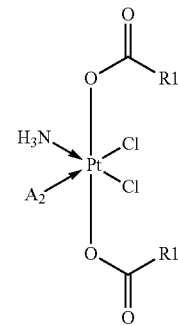

where $R_1$ is methyl and $A_2$ is either cyclohexylamine (the complex with the trade name "Satraplatin", see EP 0 328 274) or 1-adamantylamine (the complex has the code name "LA-12", see U.S. Pat. No. 6,503,943). Cyclohexylamine or 1-adamantylamine is highly lipophilic aminoligand which improves lipophility of the platinum (IV) complex and its penetration through the lipid cell membrane which results in the improvement of antitumor efficacy as a consequence. There is expert opinion that $R_1$ group preferably contains 1 to 10 carbon atoms in the aliphatic chain or 3 to 7 carbon atoms in the carbon cycle (see EP 0 328 274, p. 3, line 12 and further), more preferably 3 (see ibid, claim 3). Satraplatin and LA-12 represent the best state of the art in this type of platinum complexes which offer the possibility of per oral administration and overcome in vitro efficacy of cisplatin and cisplatin resistance, too. However, they are more than ten years in clinical testing with average results which do not confirm their very good in vitro antitumor potential.

Adamantane is tricyclo $(3.3.1.1^{3,7})$ decane which has the unique, highly lipophilic and highly symmetric structure like diamond. Adamantyl derivatives were proposed for improvement of properties of many compounds including drugs in the prior art, e.g. Chem. Rev. 2013, No. 113, 3516. Even though adamantyl derivatives offer excellent tool for the improvement of the stability and lipophility of drugs it was not yet been fully exploited in platinum (IV) complexes. There have been described only very few platinum complexes with 1-adamantyl group in the prior art, moreover, these complexes contained the only one 1-adamantyl group. It was beside LA-12 its Pt (IV) analog with "all trans" configuration of ligands (J. Inorg. Biochem. 2008, No. 102, 1077) and further Pt(II) analogues of cisplatin having 1-adamantylamine in configuration "cis" (Gynecol. Oncol. 2006, No. 102, 32) and "trans" (J. Inorg. Biochem. 2008, No. 102, 1077) which had, however, a low antitumor efficacy.

"c-t-c" platinum (IV) complexes according to formula (I) with different axial carboxylate ligands $B_1$ and $B_2$ are generally prepared by the reaction of abundance of appropriate carboxylic acid anhydride with "c-t-c" $PI(C_1,C_2)(OH)_2(A_1, A_2)$ intermediate (e.g. EP 0 328 274, examples 1 to 5; J. Med. Chem. 1997, 40, 112). The reaction usually takes several days at room temperature, yields are between 23-87% and purity is between 70-95%. The further purification is necessary to achieve purity above 98% with the yield about 68% in the case of Satraplatin (see CN 1557821). The use of more reactive chloride of carboxylic acid instead of its anhydride to decrease the reaction time is possible but the yield is 14% only (see EP 0 328 274, Example 8).

So, there is still a continuing need for new platinum (IV) complexes with improved antitumor efficacy for the therapy of tumor diseases.

SUMMARY OF THE INVENTION

According to a first aspect of the invention, there is provided a platinum (IV) complex with "cis-trans-cis" configuration of the ligands of the formula (III):

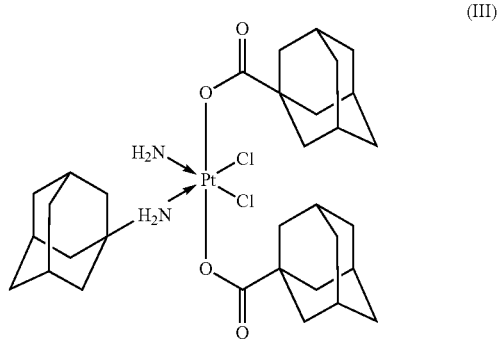

(III)

We surprisingly found that introduction of more than one 1-adamantyl group in the platinum (IV) complex of formula (II) is possible due to the bulky central Pt(IV)-ion and that the platinum (IV) complex of the formula (III) of the present invention, hereinafter also called TU-31 or "c-t-c" $PtCl_2(1$-adamantylcarboxylato$)_2(NH_3,1$-adamantylamine), significantly exceeds temporary best "c-t-c" Pt(IV) complexes Satraplatin and LA-12 in antitumor efficacy $IC_{50}$ ($IC_{50}$=half maximal inhibitory concentration of the compound which inhibits specific biological or biochemical functions). Without being bound by theory, said effects can be explained by substantially increased both lipophility and stability of TU-31 resulting in a better penetration through the lipid cell membrane and a better stability in the body by a space protection of the central Pt (IV)-ion by three bulky, highly lipophilic and symmetric 1-adamantyl groups. We tested a dependence of $IC_{50}$ of the platinum (IV) complex of the formula (II), where $R_1$ is methyl, on the structure and lipophility of the equatorial aminoligand $A_2$ and we found that there is no clear dependence but that the best results had 1-adamantylamine as the equatorial aminoligand $A_2$ (i.e. LA-12 complex). We further tested a dependence of $IC_{50}$ of the platinum (IV) complex of the formula (II) with 1-adamantylamine as the equatorial ligand $A_2$, on the structure and lipophility of the group $R_1$ in axial carboxylate ligands and we found that there is no clear dependence in accordance with the prior art but with the surprising exception of the best results with 1-adamantyl group as the group $R_1$ which is a new and surprising knowledge. We further found that 1-adamantylcarboxylate ligand itself has a low cytotoxicity and so, TU-31 also offers an improvement of the therapeutic index, too. Chlorides as physiological substances are preferred as leaving ligands in the TU-31.

TU31 has not only the best in vitro results $IC_{50}$ with respect to Satraplatin or LA-12 but it also offers improvement of "in vivo" antitumor efficacy due to substantially increased lipophility and stability.

According to a second aspect of the invention, there is provided a process for preparing of the platinum (IV) complex of the formula (III) by reaction of "c-t-c" $PtCl_2(OH)_2(NH_3,1$-adamantylamine) with 1-adamantylcarbonyl chloride and an amine in a non-polar aprotic solvent, preferably 1,4-dioxane. Preferably, the amine is pyridine or trialkylamine. Most preferred is pyridine.

Pyridine was successfully used in a prior art as both scavenger of HCl and a solvent in a reaction disclosed for example in U.S. Pat. No. 4,604,463, example 2 and 3, column 16, line 25, but we found with a surprise that the use of pyridine as a solvent severely hampers a conversion of this reaction and that 1-2 stoichiometric amounts of pyridine with respect to 1-adamantyl-carbonyl chloride are preferred to be used for successful conversion of "c-t-c" $PtCl_2(OH)_2(NH_3,1$-adamantylamine) to the platinum (IV) complex of the formula (III).

In a preferred embodiment of the present invention, a process for preparing of the platinum (IV) complex of the formula (III) is provided by reaction of 'c-t-c' $PtCl_2(OH)_2(NH_3,1$-adamantylamine) with 1-adamantylcarbonyl chloride and pyridine in a non-polar aprotic solvent, preferably 1,4-dioxan, in a stoichiometric or molar ratio of pyridine to 1-adamantylcarbonyl chloride from 1 to 2 parts of pyridine to 1 part of 1-adamantylcarbonyl chloride, preferably in a 2 to 1 ratio, preferably in a 1.5 to 1 ratio, most preferably in a 1 to 1 ratio.

$CH_2Cl_2$ was used in a prior art as a solvent for preparing of another platinum (IV) complex with the use of propionyl chloride and triethylamine as HCl scavenger but the yield was 14% only, see EP 0 328 274, example 8, p. 5, line 20. We found with a surprise that a use of 1,4-dioxane as a non-polar aprotic solvent instead of $CH_2Cl_2$ gave a very good yield and quality of the platinum (IV) complex of the formula (III).

In a preferred embodiment, the present process is carried out for 0.5 to 6 hours, preferably 1 to 5 hours, preferably 1 to 4 hours.

The present process is preferably conducted at a temperature from 19 to 26° C., preferably at 20 to 24° C., preferably at 20 to 22° C., preferably at room temperature.

Preferably, the product precipitates from the solvent and related impurities remain in the solvent.

In a preferred embodiment, the product is separated for instance by filtration or centrifugation, preferably washed by water and solvent and preferably dried under vacuum at elevated temperature. The yield of the product is preferably above 80% with a purity above 98%, preferably above 98.5%, preferably of 98.6%.

The present invention also relates to a platinum (IV) complex of the formula (III), which is obtainable, in particular obtained, by a process of the present invention.

According to the third aspect of the invention, there is provided a pharmaceutical composition for the therapy of tumor diseases containing TU-31 and at least one lipophilic and pharmaceutically acceptable additive as a binder, a carrier or a surfactant.

In a preferred embodiment of the present invention, the pharmaceutical composition is characterized by having a content of TU-31 of 0.5 to 50%, preferably 1 to 45%, preferably 5 to 40%, preferably 10 to 30% by weight based on the total weight of the composition.

We found that TU-31 is very good compatible with the most lipophilic and pharmaceutically acceptable binders, carriers or surfactants due to its high lipophility. We further found with a surprise that TU-31 is even soluble in the lipophilic and pharmaceutically acceptable binders, carriers or surfactants at elevated temperature, preferably in Gelucire 50/13 (also called stearoyl macrogol-32 glycerides) as preferred surfactant at temperature about 60° C. This hot melt solution and/or suspension result in the solid solution and/or suspension of the TU-31 in Gelucire 50/13 after its cooling. The proportion of the solution and/or suspension in the composition depends on the content of TU-31 in Gelucire 50/13. Surfactant Gelucire 50/13 also protects TU-31 against the aggressive action of hydrophilic gastric juice in the digestive tract, in particular in stomach, after oral administration. We confirmed the stability of TU-31 in the composition with the surfactant Gelucire 50/13 in 0.1 N—HCl at 37° C. during at least 1 hour. Further, the surfactant Gelucire 50/13 entirely, or at least partially, emulgates TU-31 into the outer hydrophilic phase of the digestive tract which increase bioavailability of TU-31 from gastrointestinal system after oral administration. The resulting solid pharmaceutical composition comprising TU-31 and Gelucire 50/13 can be disintegrated by generally known procedures and then enclosed in a hard gelatin or hydroxypropyl methyl cellulose capsules or in soft gelatin capsules or pearls. The present invention also provides in a preferred embodiment a liquid pharmaceutical composition, preferably an aqueous emulsion of TU-31 in Gelucire 50/13.

Thus, in a preferred embodiment of the present invention, a pharmaceutical composition is provided comprising the platinum (IV) complex of formula (III) of the present invention and stearoyl macrogol-32 glycerides (Gelucire 50/13).

Addition of an inert solid excipients, e.g. microcrystallic cellulose, can be further contemplated to achieve a desired physical properties of the composition.

In a preferred embodiment, the pharmaceutical composition according to the invention is intended for the treatment of tumor diseases, preferably malignant tumors, preferably by oral administration.

Accordingly, in a preferred embodiment the present platinum complex of formula (III) and/or the present composition may be formulated in form of solutions, suspensions, capsules, tablets, pills, and so on, preferably in sterile form.

According to a further aspect of the invention, the present platinum (IV) complex of formula (III) is provided for use in a method to treat tumor diseases.

In a further aspect of the present invention, a method of treating tumor diseases in a subject in need thereof is provided, comprising administering the present pharmaceutical composition or the platinum (IV) complex of formula (III) to a patient in need thereof in a suitable dosage and dosage regimen so as to obtain an effective treatment of the tumor disease.

Further preferred embodiments are the subject-matter of the dependent claims.

The invention is further explained and illustrated, but not limited, by the following examples of embodiment.

EXAMPLE 1

Synthesis of Platinum (IV) Complexes According to the Formula (II) and (III)

a) Synthesis of Key Intermediates "c-t-c" $PtCl_2(OH)_2(NH_3$, Alkyl- or Cykloalkylamine or Polycykloalkylamine)

The synthesis was carried out according to general procedure described in the U.S. Pat. No. 6,503,943, example 2a, column 4, line 45 and further.

b) Synthesis of "c-t-c" $PtCl_2(Alkylcarboxylato)_2(NH_3$, Alkyl- or Cycloalkylamine or Polycycloalkylamine), i.e. the Platinum (IV) Complexes According to the Formula (II)

The synthesis was carried out according to the general procedure described in EP 0 328 274, examples 1 to 5, page 4.

c) Synthesis of TU-31, i.e. "c-t-c" $PtCl_2$(1-Adamantylcarboxylato)$_2$(NH$_3$,1-Adamantylamine)

The synthesis was carried in the absence of light 1.0 g of "c-t-c" $PtCl_2OH(NH_3$,1-adamantylamine) with purity 99% (2.1 mmol), 20 ml of 1,4-dioxane with purity >99%, 1.05 ml of pyridine with purity>99% (12.9 mmol) and 2.2 g of 1-adamantanecarbonyl chloride with purity >95% (10.5 mmol) were stirred 3 hours at room temperature. The resulting mixture was allowed to stand at room temperature for 8 hours. Precipitated TU-31 was separated by filtration, washed repeatedly by water and 1,4-dioxane and then it was dried in vacuum at 45° C. The yield of the TU-31 was 1.43 g (86% based on the theory) and the purity was 98.6% (by HPLC).

EXAMPLE 2

Preparation of a Pharmaceutical Composition of TU-31, i.e. "c-t-c" $PtCl_2$(1-Adamantylcarboxylato)$_2$ (NH$_3$,1-Adamantylamine) with Gelucire 50/13

1.0 g of TU-31 and 4.0 g of Gelucire 50/13 were heated to 65° C. to create a yellow melt. This melt was poured into polypropylene mold and cooled 1 hour at −18° C. Solid composition was then mechanically grated into particles, each weighing approximately 5 mg and containing 20% by weight of the TU-31. The grated composition was filed into hydroxypropyl methyl cellulose capsules with a dosage 1.0 g of the composition containing 200 mg of the active substance per each capsule.

EXAMPLE 3

Determination of In Vitro Cytotoxicity $IC_{50}$ of Prepared Platinum (IV) Complexes Abbreviation of Used Compounds DMSO: dimethyl sulfoxide
PBS: phosphate buffered saline
XTT: 2,3-bis-(2-methoxy-4-nitro-5-sulphophenyl)-2H-tetrazolium-5-carboxanilide salt
PMS: N-methyl-dibenopyrazinmethylsulfate
FBS: fetal bovine serum
NEAA: non-essential amino acids
L-glu: L-glutamine
DMEM: Dulbecco's Modified Eagle's Medium (SigmaAldrich)
PMS: phenazine methosulfate
Tested Compounds:
Platinum (IV) Complexes According to the Specification in the Tables
Used Tumor Cell Lines:
MCF-7 breast adenocarcinoma
CaCo-2 colon adenocarcinoma
HL60 promyelotic leukaemia
A2780/cis ovarian carcinoma cisplatin resistant
LNCaP prostate cancer
COR-L23 lung carcinoma
Cultivation's conditions: 37° C., 5% $CO_2$
Growth medium: DMEM, 10% FBS, 2 mM L-glut., NEAA 100×

Working Procedure:

Tested compounds were dissolved in DMSO and diluted by PBS to tested concentration range just before addition to cell lines in wells. PBS was used as a positive control, DMSO in final concentration 20% was used as a negative control. All concentrations of compounds were assayed in triplicates. Each determination was carried out twice and was blinded for experimenter. Testing was conducted on a 96-well plate. Dosage of tumor cells was about $2.5 \times 10^4$ cells per well, dosage of growth medium was 100 µl per well. After 24 hours, the growth medium was suck off and 80 µl of fresh growth medium and 20 µl of solution with different concentration of the tested substance were added to wells. After 72 hours, the medium was suck off and 100 µl of a solution of Optimem reagent containing XTT and PMS were added to wells. After another 4 hours, the absorbance was measured at 450 nm (reference was at 630 nm). Results as ICs, were evaluated from the graph of normalized viability of cells plotted against the logarithm of the concentration of the substance.

EXAMPLE 4

Study of a Dependence of IC of Platinum (IV) Complexes According to the Formula (II) on the Structure and Lipophily of the Equatorial Aminoligand $A_2$, Wherein the $R_1$ Group is Methyl Platinum (IV) complexes according to the formula (U) where $R_1$ group is methyl and $A_2$ group is different aminocompound were prepared according to the example 1. Tumor cell lines MCF-7 (breast adenocarcinoma) and CaCo-2 (colon adenocarcinoma) were used. $IC_{50}$ were measured according to procedure in the example 3. Commercially available cisplatin and oxaliplatin were used as reference compounds. The results are shown in the Table 1.

TABLE 1

A study of dependence of $IC_{50}$ of platinum (IV) complexes according to the formula (II) on the structure and lipophility of the equatorial aminoligand $A_2$, $R_1$ group is methyl

| | | | $IC_{50}$ (µmol) | |
|---|---|---|---|---|
| No. of Pt(IV) complex | $R_1$ group in axial ligands | The equatorial aminoligand $A_2$ | MCF-7 tumor cell line | CaCo-2 tumor cell line |
| 1. | $CH_3$— | $NH_3$ | 137.0 | 56.1 |
| 2. | $CH_3$— | $H_3C-\underset{\underset{CH_3}{\vert}}{\overset{\overset{CH_3}{\vert}}{C}}-NH_2$ | 168.0 | 71.3 |
| 3. (Satraplatin) | $CH_3$— | 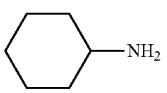 | 27.2 | 12.7 |
| 4. (LA-12) | $CH_3$— | 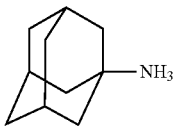 [SMILES: NC12CC3CC(CC(C3)C1)C2] | 9.6 | 9.3 |

TABLE 1-continued

A study of dependence of IC$_{50}$ of platinum (IV) complexes according to the formula (II) on the structure and lipophility of the equatorial aminoligand A$_2$, R$_1$ group is methyl

| No. of Pt(IV) complex | R$_1$ group in axial ligands | The equatorial aminoligand A$_2$ | IC$_{50}$ (μmol) MCF-7 tumor cell line | IC$_{50}$ (μmol) CaCo-2 tumor cell line |
|---|---|---|---|---|
| 5. | CH$_3$— | 2-adamantyl-NH$_2$ | 18.3 | 109.4 |
| 6. | CH$_3$— | 1-adamantyl-C(CH$_3$)H-NH$_2$ | 45.5 | 39.3 |
| 7. | CH$_3$— | 3,5-dimethyl-1-adamantyl-NH$_2$ | 317.8 | 478.5 |
| 8. | CH$_3$— | diamantyl-NH$_2$ | 9.5 | 104.6 |
| 9. | CH$_3$— | triamantyl-NH$_2$ | 45.6 | 14.0 |
| 10. | — | Reference-Cisplatin Pt(II) complex | 53.4 | 70.5 |
| 11. | — | Reference-Oxaliplatin Pt(II) complex | 46.5 | 55.7 |

It follows from the results in the Table 1:

1. There is no clear relationship between type and lipophility of the equatorial aminoligand A$_2$ and IC$_{50}$.
2. The best results has the platinum (IV) complex with 1-adamantylamine equatorial ligand which is in accordance with the prior art.
3. A change of 1-adamantyl skeleton to 3,5-dimethyl-1-adamantyl skeleton results in worsening of antitumor efficacy, probably due to worsening of the symmetry of 1-adamantyl group. A high symmetry of 1-adamantane skeleton like diamonds is probably important in this type of platinum (IV) complexes.
4. A change of 1-adamantyl skeleton to 2-adamantyl skeleton results also in worsening of antitumor efficacy, probably due to worsening of a space protection of central Pt(IV)-ion.
5. An increase of distance between 1-adamantane skeleton and central Pt(IV)-ion results in worsening of antitumor efficacy, probably due to worsening of a space protection of central Pt(IV)-ion.

EXAMPLE 5

Study of a Dependence of IC$_{50}$ of Platinum (IV) Complexes According to the Formula (II) on the Structure and Lipophility of the Group R$_1$, Equatorial Aminoligand A$_2$ is 1-Adamantylamine Platinum (IV) complexes according to the formula (II) where A$_2$ is 1-adamantylamine and the R$_1$ group is different alkyl or 1-adamantyl were prepared according to the example 1. Tumor cell lines MCF-7 (breast adenocarcinoma) and CaCo-2 (colon adenocarcinoma) were used. IC$_{50}$ was measured according to procedure in the example 3. The results are shown in the Table 2.

TABLE 2

A study of dependence of $IC_{50}$ of platinum (IV) complexes according to the formula (II) on the structure and lipophility of the axial group $R_1$, the equatorial aminoligand $A_2$ is 1-adamantylamine.

| No. of Pt(IV) complex | Ligand $A_2$ | Group $R_1$ | $IC_{50}$ (µmol) MCF-7 | CaCo-2 |
|---|---|---|---|---|
| 1. | 1-adamantyl-NH$_2$ | $CH_3$— | 9.6 | 9.3 |
| 2. | 2-adamantyl-NH$_2$ | $(CH_3)_3C$— | 5.4 | 4.5 |
| 3. | 2-adamantyl-NH$_2$ | $CH_3(CH_2)_6$— | 10.0 | 10.2 |
| 4. | 2-adamantyl-NH$_2$ | $CH_3(CH_2)_{10}$— | 39.2 | 67.1 |
| 5. | 2-adamantyl-NH$_2$ | 2-adamantyl- | 4.1 | 1.9 |

It follows from the results in the Table 2:
1. There is no clear relationship between number of carbon atoms in the aliphatic chain of $R_1$ group. The LA-12 with methyl group as $R_1$ had a good results but platinum complex with tert-butyl group as $R_1$ appears the best among all tested aliphatic chains which is in accordance with the prior are (see EP0328274, the claim 1-3).
2. 1-Adamantyl group surprisingly exceeds all tested groups $R_1$ including tert-butyl group.

EXAMPLE 6

Comparison of $IC_{50}$ of the TU-31, i.e. the Platinum (IV) Complex of the Formula (III), with Referent Platinum (II) Complex Oxaliplatin and the Temporary Best Platinum (IV) Complex LA-12 on the Broader Tumor Cell Line Panel Tested Tumor Cell Line Panel:
MCF-7 breast adenocarcinoma
CaCo-2 colon adenocarcinoma
HL60 promyelotic leukaemia
A2780/cis ovarian carcinoma cisplatin resistant
LNCaP prostate cancer
COR-L23 lung carcinoma

TABLE 3

A comparison of $IC_{50}$ of TU-31, that means the platinum (IV) complex of formula (III), with referent platinum (II) complex oxaliplatin and the temporary best platinum (IV) complex LA-12 on the broader tumor cell line panel.

| Type of platinum complex | $IC_{50}$ (µmol) | | | | | |
|---|---|---|---|---|---|---|
| | MCF-7 | CaCo-2 | HL-60 | A2780/cis | LNCaP | COR-L23 |
| Oxaliplatin Pt(II)complex | 46.5 | 55.7 | 0.4 | >132 | 0.5 | >141 |
| LA-12 Pt(IV)complex | 9.6 | 9.3 | 0.2 | 8.6 | 1.8 | 6.1 |
| TU-31 Pt(IV)complex | 4.1 | 1.9 | 0.1 | 1.5 | 4.8 | 8.0 |

It follows from the results in the Table 3:
1. The TU-31, i.e. the platinum (IV) complex according to invention, exceeds the best platinum (II) complex oxaliplatin and temporary the best platinum (IV) complex LA-12 in four of the six tested cancer cell lines.
2. Oxaliplatin had better result in the tumor cell line LNCaP where antitumor efficacy is decreased with increased lipophility of the platinum complex.

The invention claimed is:

1. A platinum (IV) complex with "cis-trans-cis" configuration of the ligands of the formula (III):

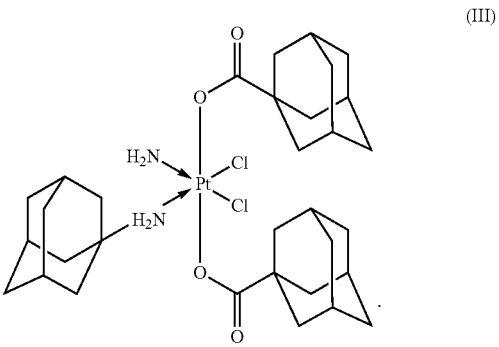

(III)

2. A process for preparing the platinum (IV) complex according to claim 1 by the reaction of "cis-trans-cis" $PtCl_2((OH)_2(NH_3,1\text{-adamantylamine})$ with 1-adamantylcarbonyl chloride and an amine in a non-polar aprotic solvent.

3. The process according to claim 2, wherein the non-polar aprotic solvent is 1,4-dioxane.

4. The process according to claim 2, wherein the amine is pyridine or trialkylamine.

5. The process according to claim 2, wherein the amine is pyridine and wherein the stoichiometric ratio of pyridine to 1-adamantyl-carbonyl chloride is from 1 to 2 parts pyridine to 1 part 1-adamantylcarbonyl chloride.

6. A pharmaceutical composition for the therapy of tumor diseases containing the platinum (IV) complex according to claim 1 and at least one lipophilic and pharmaceutically acceptable additive.

7. The pharmaceutical composition of claim 6, in which composition the content of the platinum (IV) complex according to claim 1 is 0.5 to 50% by weight based on the total Weight of the composition.

8. The pharmaceutical composition according to claim 6, wherein the additive is stearoyl macrogol-32 glycerides.

9. The process according to claim 3, wherein the amine is pyridine or trialkylamine.

10. The process according to claim 3, wherein the amine is pyridine and wherein the stoichiometric ratio of pyridine to 1-adamantyl-carbonyl chloride is from 1 to 2 parts pyridine to 1 part 1-adamantylcarbonyl chloride.

11. The process according to claim 4, wherein the stoichiometric ratio of pyridine to 1-adamantyl-carbonyl chloride is from 1 to 2 parts pyridine to 1 part 1-adamantylcarbonyl chloride.

12. A method for treating a tumor disease in a patient affected by such disease comprising administering an effective anti-tumor amount of the compound of claim 1 in a pharmaceutically acceptable vehicle.

13. A method according to claim 12, wherein the vehicle is lipophilic.

14. The pharmaceutical composition according to claim 7, wherein the additive is stearoyl macrogol-32 glycerides.

15. A method for treating a tumor in a patient in need of such treatment comprising administering a pharmaceutical composition containing an effective anti-tumor amount of a platinum (IV) complex with cis-trans-cis configuration of the ligands of the formula (III):

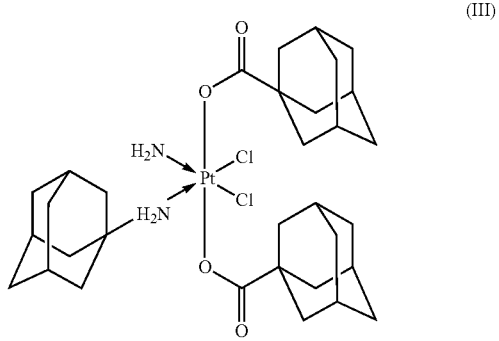

in a pharmaceutically acceptable vehicle, wherein the effective amount of the platinum complex is 0.5 to 50% by weight of the total weight of the composition.

* * * * *